United States Patent [19]

Gauthier et al.

[11] Patent Number: 4,521,534

[45] Date of Patent: Jun. 4, 1985

[54] IMIDAZO[2,1-A]PYRROLO[2,1-c][1,4]BENZODIAZEPINE DERIVATIVES, METHODS OF PREPARATION AND USE

[75] Inventors: Jean A. Gauthier, Montreal; Katherine Voith, Dorval; André A. Asselin, St. Laurent, all of Canada

[73] Assignee: Ayerst, McKenna & Harrison, Ltd., Montreal, Canada

[21] Appl. No.: 562,905

[22] Filed: Dec. 19, 1983

[51] Int. Cl.³ .................. A61K 31/55; C07D 487/22
[52] U.S. Cl. .................................. 514/219; 260/245.6; 544/58.4; 544/139; 544/370; 546/199

[58] Field of Search ................... 260/245.6; 544/58.4, 544/139, 370; 546/199; 424/246, 248.5, 250, 267, 273 R

[56] References Cited

U.S. PATENT DOCUMENTS 4,352,815 10/1982 Hunkeler et al. .............. 424/273 R
4,352,818 10/1982 Hunkeler et al. .............. 424/273 R

*Primary Examiner*—Richard L. Raymond

[57] ABSTRACT

This invention discloses novel imidazo[2,1-a]pyrrolo[2,1-c][1,4]benzodiazepine derivatives, processes for their preparation, pharmaceutical compositions thereof and methods for using the compounds. The compounds of this invention are useful as antiobesity agents to reduce food intake in a mammal.

16 Claims, 1 Drawing Figure

THE FOLLOWING REACTION SCHEME ILLUSTRATES A METHOD FOR PREPARING THE COMPOUNDS OF FORMULA I.

IMIDAZO[2,1-A]PYRROLO[2,1-C][1,4]BENZODIAZEPINE DERIVATIVES, METHODS OF PREPARATION AND USE

BACKGROUND OF THE INVENTION

This invention relates to novel imidazo[2,1-a]pyrrolo[2,1-c][1,4]benzodiazepine derivatives, to processes for their preparation, to methods of using the derivatives and to pharmaceutical compositions of the derivatives. The compounds of this invention are useful as antiobesity agents.

The compounds of this invention have a novel imidazo[2,1-a]pyrrolo[2,1-c][1,4]benzodiazepine ring system. The closest related and known ring system is illustrated by the imidazo[1,5-a]pyrrolo[2,1-c][1,4]benzodiazepine derivatives described by W. Hunkeler et al., U.S. Pat. No. 4,352,818, Oct. 5, 1982 and U.S. Pat. No. 4,352,815, Oct. 5, 1982. The compounds of this invention are distinguished from the known compounds by having a different ring system, different substituents on the ring system and different pharmacological activity.

SUMMARY OF THE INVENTION

The compounds of this invention are represented by formula I

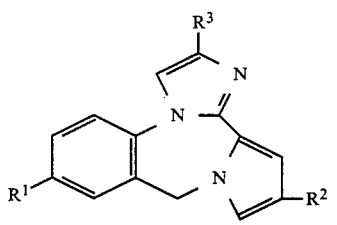

in which $R^1$ is hydrogen, halo or lower alkyl; $R^2$ is hydrogen or CS-$R^4$ wherein $R^4$ is 4-morpholinyl, 4-thiomorpholinyl, 1-pyrrolidinyl, 1-piperidinyl, 4-(lower alkyl)-1-piperazinyl, 4-(4-fluorophenyl)-1-piperazinyl; and $R^3$ is hydrogen or lower alkoxycarbonyl; or a therapeutically acceptable acid addition salt thereof.

A preferred group of compounds is represented by formula I in which $R^1$ is hydrogen, chloro or lower alkyl; $R^2$ is hydrogen or CS-$R^4$ wherein $R^4$ is 4-morpholinyl, 4-thiomorpholinyl, 1-pyrrolidinyl, 4-(lower alkyl)-1-piperazinyl or 4-(4-fluorophenyl)-1-piperazinyl; and $R^3$ is hydrogen or lower alkoxycarbonyl; with the proviso that when $R^2$ is CS-$R^4$ then $R^3$ is hydrogen; or a therapeutically acceptable acid addition salt thereof.

A more preferred group of compounds is represented by formula I in which $R^1$ is hydrogen, chloro or methyl; $R^2$ is hydrogen or CS-$R^4$ wherein $R^4$ is 4-morpholinyl, 4-thiomorpholinyl or 4-(4-fluorophenyl)-1-piperazinyl with the proviso that when $R^2$ is CS-$R^4$ then $R^3$ is hydrogen; or a therapeutically acceptable acid addition salt thereof.

The compounds of this invention form a pharmaceutical composition which comprises a compound of formula I, or a therapeutically acceptable acid addition salt thereof, and a pharmaceutically acceptable carrier.

The compounds of this invention are antiobesity agents, having the capacity to suppress the appetite and reduce food consumption in a mammal. Hence, a method for reducing food intake in a mammal is provided which comprises administering to the mammal an effective food-intake reducing amount of a compound of formula I, or a therapeutically acceptable acid addition salt thereof.

DETAILED DESCRIPTION OF THE INVENTION

Figure 1:
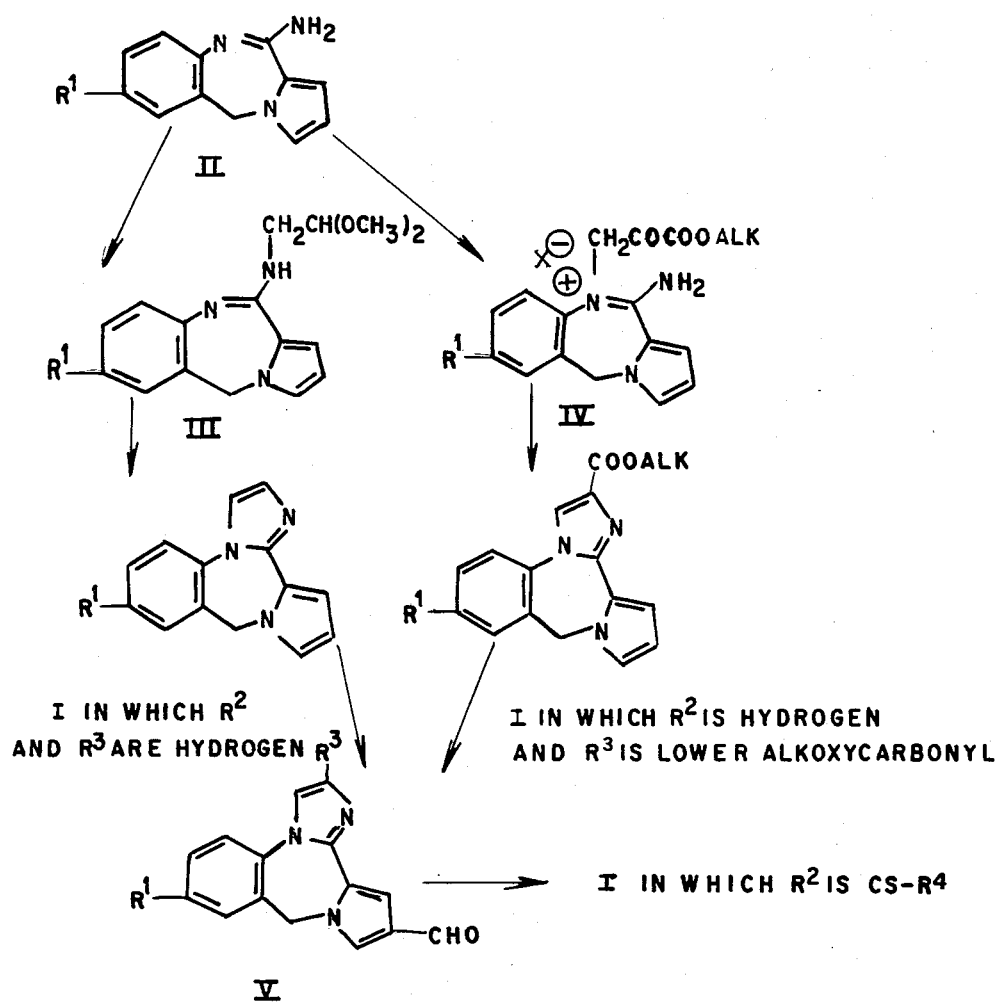

The term "lower alkyl" as used herein means straight and branched chain alkyl radicals containing from one to six carbon atoms, preferably one to four carbon atoms, and includes methyl, ethyl, propyl, 1-methylethyl, butyl, 1,1-dimethylethyl, pentyl and the like, unless stated otherwise.

The term "halo" as used herein means halo radicals and includes fluoro, chloro, bromo and iodo, unless stated otherwise.

The term "lower alkoxy" as used herein means straight chain alkoxy radicals containing from one to six carbon atoms and branched chain alkoxy radicals containing three to six carbon atoms and includes methoxy, ethoxy, 1-methylethoxy, butoxy, hexoxy and the like.

The term "lower alkanol" as used herein means both straight and branched chain alkanols containing from one to four carbon atoms and includes methanol, ethanol, 1-methylethanol, butanol and the like.

The term "organic proton acceptor" as used herein means the organic bases or amines, for instance, triethylamine, pyridine, N-ethylmorpholine, 1,5-diazabicyclo[4.3.0]non-5-ene and the like.

The term "inorganic proton acceptor" as used herein means the inorganic bases, preferably the alkali methyl hydroxides, carbonates and bicarbonates, for example, sodium hydroxide, potassium hydroxide, sodium carbonate, sodium bicarbonate, potassium carbonate and the like.

The term "proton acceptor" as used herein means a proton acceptor selected from an organic proton acceptor and inorganic proton acceptor, as defined hereinabove.

The compounds of this invention are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture.

These salts, when administered to a mammal, possess the same pharmacologic activities as the corresponding bases. For many purposes it is preferable to administer the salts rather than the basic compounds. Suitable acids to form these salts include the common mineral acids, e.g. hydrohalic, sulfuric or phosphoric acid; the organic acids, e.g. maleic, citric or tartaric acid; and acids which are sparingly soluble in body fluids and which impart slow-release properties to their respective salts, e.g. pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

When the compounds of formula I of this invention are used as antiobesity agents for reducing or controlling food consumption in a mammal, they are used alone or in combination with pharmacologically acceptable carriers, the proportion of which is determined by the solubility and the chemical nature of the compound, chosen route of administration and standard biological practice.

For example, they are administered orally in solid form i.e. capsule or tablet. They can also be administered orally in the form of suspensions or solutions or they may be injected parenterally. They also can be administered in a mixture with the feed for the mammal.

The tablet compositions for oral administration contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I for oral administration contain the active ingredient in admixture with one or more nontoxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions for oral administration can be formulated by suspending the active ingredient in ethyl alcohol, in a vegetable oil, for example, arachis oil, olive oil, sesame oil, or coconut oil, or in a mineral oil, for example liquid paraffin, and the suspension may contain a thickening agent, for example beeswax or hard paraffin. These compositions can also contain a sweetening agent, flavoring agent and antioxidant.

For administration to a mammal by parenteral injection, it is preferred to use the compounds of formula I in solution in a sterile aqueous vehicle which may also contain other solutes, such as buffers or preservatives, as well as sufficient quantities of pharmaceutically acceptable salts or of glucose to make the solution isotonic.

The compounds of the present invention may be blended into the feed of the mammal by standard techniques. Compositions can be formed by finely grinding or pulverizing the active ingredient and the feed using any commercially available grinder or pulverizer. The active ingredient may be compounded or blended with a feed additive, premix, feed concentrate or feed additive supplement to form a dietary composition for eventual administration to a mammal. A feed additive, concentrate or premix is a composition to be diluted to produce a complete feed. The latter composition contains any suitable carrier or extender material which is inert to the active material and is non-toxic to the mammal.

The dosage of the compounds of formula I as antiobesity agents will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under circumstances is reached. In general, the compounds of this invention are most desirably administered at a concentration level that will generally afford effective results without causing any harmful or deleterious side effects. For example, an effective antiobesity amount of a compound of formula I usually ranges from about 10 mg to about 100 mg per kg of body weight per day in single or divided doses, although as aforementioned, variations will occur. However, a dosage level that is in the range of from about 10 mg to about 50 mg per kg of body weight per day in single or divided dose is employed most desirably in order to achieve effective results.

The antiobesity properties of the compounds of formula I, namely the ability of the compounds to reduce food intake in a mammal, can be demonstrated in standard pharmacological tests; for example, in the conditioned food-intake test.

More explicitly, and by way of an example, the food-intake test is conducted as follows:

Male albino Sprague-Dawley rats (obtained from the Canadian Breeding Laboratories, St. Constant, Quebec, Canada), weighing 150–160 grams, are individually caged and exposed to powdered purina lab chow ad libitum for six days as a period of adjustment to the metabolic cages and powdered food.

The metabolic cages (internal size $10 \times 12 \times 19$ cm) were furnished with detachable metal food-cups designed to minimize spillage of food (powdered) purina lab chow) and with removable lids to control the feeding schedule.

At 3 p.m. on the sixth day the food cups are covered with lids. The animals are allowed to eat for only three hours per day between 12:00 a.m. and 3:00 p.m. with free access to water. After the animals have been maintained on this feeding schedule for two days, the food intake on the third day is determined by measuring the difference between the initial and final food cup weights after three hours (at 3:00 p.m.).

The day before the test day, all the animals are weighed before the feeding and injected i.p. with vehicle 30 min. before feeding time, and food intake is measured after one and three hours (1:00 p.m. and 3:00 p.m.). Each time after the three hour measurements have been taken, the food cups are filled to the initial weights and covered. Rats whose body weights or food intakes are much higher or lower than those of the majority of the test colony are excluded. The remaining rats are divided into groups according to body weights and food intakes at both one and three hours, i.e., all groups have similar mean body weights and food intakes at one and three hours.

On the test day, the body weights of all groups of animals are taken and then they are injected i.p. or p.o. with either vehicle or test compounds 30 or 60 minutes, respectively before feeding. The amounts eaten after one and three hours are measured. Food eaten by the groups injected with test compounds (treatment groups) are compared with the amount eaten by the group injected with vehicle (control group). The percent decrease in food consumed when the treatment groups are compared to the control group is used to determine the anorectic activity of each test compound.

The following table illustrates the results obtained when representative compounds of formula I were evaluated in the preceding test at a dose of 30 mg/kg, i.p.

| Compound of Formula I | | | Example In Which Compound is Prepared | Food intake, % decrease at 1-hr |
|---|---|---|---|---|
| $R^1$ | $R^2$ | $R^3$ | | |
| H | H | H | 1 | 51* |
| H | H | COOEt | 2 | 40* |
| Me | H | COOEt | 2 | 63* |
| Cl | H | COOEt | 2 | 60* |
| H | CS—N(CH$_2$CH$_2$)$_2$O | H | 3 | 88*** |
| H | CS—N(CH$_2$CH$_2$)$_2$S | H | 3 | 61*** |
| H | CS—N(CH$_2$CH$_2$CH$_2$CH$_2$) (pyrrolidine) | H | 3 | 47** |
| H | CS—N(CH$_2$CH$_2$)$_2$N—Me | H | 3 | 40** |
| H | CS—N(CH$_2$CH$_2$)$_2$N—C$_6$H$_4$—F | H | 3 | 61*** |

*$P < 0.05$
**$P < 0.01$
***$P < 0.001$

FIG. 1 illustrates a method for preparing the compounds of formula I.

With reference to FIG. 1, most of the starting materials of formula II are described by W. B. Wright et al., J. Med. Chem., 23,462 (1980) or they can be prepared in an analogous manner.

The compounds of formula I in which $R^1$ is as defined herein and $R^2$ and $R^3$ are each hydrogen are prepared by condensing the appropriate starting material of formula II in which $R^1$ is as defined herein with aminoacetaldehyde dimethylacetal to obtain the corresponding compound of formula III in which $R^1$ is defined herein, and cyclizing the latter compound to obtain the corresponding compound of formula I in which $R^1$ is as defined herein and $R^2$ and $R^3$ are hydrogen. For the condensation, the compound of formula II is condensed with about four to ten molar equivalents of aminoacetaldehyde dimethylacetal in the presence of about 1.5 to 2.5 molar equivalents of ammonium chloride in an inert organic solvent, preferably toluene, at about 90° to 115° C. for about two to six hours to obtain the corresponding compound of formula III in which $R^1$ is as defined herein. Cyclization of the compound of formula III is achieved by treatment with a dilute aqueous mineral acid, preferably 2N hydrochloric acid, at about 75° to 100° C. for about two to five hours to obtain the corresponding compound of formula I in which $R^1$ is as defined herein, and $R^2$ and $R^3$ are hydrogen.

For the preparation of the compounds of formula I in which $R^3$ is lower alkoxycarbonyl, the compound of formula II is condensed with a lower alkyl ester of bromo- or chloropyruvic acid to give the corresponding compound of formula IV in which $R^1$ is as defined herein, Alk is lower alkyl and $X^-$ is bromide or chloride, respectively; and cyclizing the compound of formula IV to obtain the corresponding compound of formula I in which $R^1$ is as defined herein, $R^2$ is hydrogen and $R^3$ is lower alkoxycarbonyl. The condensation of the compound of formula II with the lower alkyl ester of bromo- or chloropyruvic acid can be accomplished effectively by employing about two to five molar equivalents of the ester in an inert organic solvent, preferably dimethoxyethane or tetrahydrofuran, at about 15° to 30° C. for about one to five hours. The condensation product, namely the corresponding compound of formula IV in which $R^1$, $X^-$ and Alk are as defined herein, is then cyclized at about 70° to 90° C. in an inert organic solvent, preferably ethanol, for about one to three hours to give the corresponding compound of formula I in which $R^1$ is as defined herein, $R^2$ is hydrogen, and $R^3$ is lower alkoxycarbonyl.

If desired, the compounds of formula I in which $R^1$ and $R^3$ are defined herein and $R^2$ is hydrogen can be transformed to the corresponding compounds of formula I in which $R^1$ and $R^3$ are as defined herein and $R^2$ is CS-$R^4$ wherein $R^4$ is as defined herein. This transformation is accomplished by reacting the compound of formula I in which $R^2$ is hydrogen with Vilsmeier reagent to obtain the corresponding formyl derivative of formula V in which $R^1$ and $R^3$ are as defined herein; followed by reacting the latter formyl derivative with sulphur and the appropriate amine represented by $R^4$H wherein $R^4$ is as defined herein. More specifically, the compound of formula I in which $R^1$ and $R^3$ are as defined herein, and $R^2$ is hydrogen is reacted with an excess of a mixture of phosphoryl chloride in dimethylformamide at about 100° to 130° C. for about one to five hours. Thereafter, the reaction mixture is decomposed with water and the corresponding compound of formula V in which $R^1$ and $R^3$ are as defined herein is obtained. Treatment of the latter compound with an excess of sulphur and the amine at about 76° to 100° C. for about one to five hours gives the corresponding compound of formula I in which $R^1$ and $R^3$ are as defined herein, and $R^2$ is CS-$R^4$ wherein $R^4$ is as defined herein.

The following examples illustrate further the invention.

EXAMPLE 1

9H-Imidazo[1,2-a]pyrrolo[2,1-c][1,4]benzodiazepine (I: $R^1$, $R^2$ and $R^3$=H)

11-Amino-5H-pyrrolo[2,1-c][1,4]benzodiazepine (described by W. B. Wright et al., J. Med. Chem., 23,462 (1980), 2.00 g, 10.1 mmol) and ammonium chloride (200 mg, 19 mmol) were stirred in dry toluene (50 mL) in the presence of aminoacetaldehyde dimethylacetal (8.8 mL) under refluxing conditions for 3 hr. The precipitate which formed in the beginning redissolved to afford a brown solution. The reaction mixture was cooled in ice-water, washed with 10% (v/v) aqueous sodium hydroxide and then with brine, dried and evaporated to yield an oily residue. Crystallization of the residue from cyclohexane-hexane gave [(5H-pyrrolo[2,1-c][1,4]benzodiazepin-11-yl)amino]acetaldehyde dimethylacetal (2.41 g), mp 132°-132.5° C.; Anal. Calcd for $C_{16}H_{19}N_3O_2$: C, 67.34% H, 6.71% N, 14.73%, Found: C, 67.11% H, 6.69% N, 14.40%.

The latter compound (6.00 g, 21.0 mmoles) was stirred in boiling hydrochloric acid (2N, 200 mL) for 3 hr. The cold mixture was basified using 10% (v/v) aqueous sodium hydroxide. Several extractions of the basic mixture with chloroform gave a solid, after the washing of extracts with brine, drying and evaporation of solvent. The crude material was recrystallized from benzenehexane to afford the title compound (4.16 g): mp 202°-203° C.; Anal. Calcd for $C_{14}H_{11}N_3$: C, 75.99% H, 5.01% N, 18.99%, Found: C, 76.02% H, 5.09% N, 19.01%; NMR (CDCl$_3$)δ4.95 (s, 2H), 6.15 (t, 1H), 6.7 (m, 2H), 7.3 (m, 6H); UVmax (MeOH) 296 nm (ε8,960), 234 (17,680).

EXAMPLE 2

9H-Imidazo[1,2-a][1,4]benzodiazepine-2-carboxylic Acid, Ethyl Ester (I: $R^1$ and $R^2$=H and $R^3$=ethoxycarbonyl)

11-Amino-5H-pyrrolo[2,1-c][1,4]benzodiazepine (2.50 g, 12.7 mmol) was stirred at room temperature in dry dimethoxyethane (50 mL) in the presence of ethyl bromopyruvate (5 mL). After the 2 hr, the mixture was saturated with hexane to form a yellow powder which precipitated out of the media. This material was collected and triturated in diethyl ether, recrystallized from methylene chloride-diethyl ether to yield a pale yellow powder (2.56 g), mp 120° C., of 11-amino-10-(3-ethoxy-2,3-dioxopropyl)-5H-pyrrolo[2,1-c][1,4]benzodiazepinium bromide.

The latter salt (1.10 g, 2.80 mmoles) was stirred in boiling ethanol (50 mL) for 1 hr. The solution was evaporated to afford a solid residue which was dissolved in methylene chloride. The solution was washed with aqueous sodium hydroxide. The organic layer was saturated with hexane to yield an off-white powder of the title compound (0.56 g): mp 134°-135° C.; Anal. Calcd for $C_{17}H_{15}N_3O_2$: C, 69.61% H, 5.15% N, 14.33%, Found: C, 70.15% H, 5.22% N, 14.32%; UV max (MeOH) 279 nm (ε14,850), 236 (22,750); NMR (CDCl$_3$)δ1.4 (t, 3H), 4.4 (q, 2H), 5.0 (s, 2H), 6.15 (m, 1H), 6.8 (m, 2H), 7.35 (m, 4H), 8.00 (s, 1H).

In the same manner but replacing 11-amino-5H-pyrrolo[2,1-c][1,4]benzodiazepine with an equivalent amount of 11-amino-7-chloro-5H-pyrrolo[2,1-c][1,4]benzodiazepine or 11-amino-7-methyl-5H-pyrrolo[2,1-c][1,4]benzodiazepine, the following compounds of formula I were obtained, respectively: 7-chloro-9H-imidazo[1,2-a]pyrrolo[2,1-c][1,4]benzodiazepine-2-carboxylic acid, ethyl ester: mp 234°-235° C. (cryst. from benzene-hexane); Anal. Calcd for $C_{17}H_{14}ClN_3O_2$: C, 62.29% H, 4.30% N, 12.82%, Found: C, 62.18% H, 4.32% N, 12.76%; UV max (MeOH) 278 nm (ε14,450), 243 (29,250); NMR (CDCl$_3$)δ1.4 (t, 3H), 4.42 (q, 2H), 4.95 (s, 2H), 7.1 (m, 7H); and 7-methyl-9H-imidazo[1,2-a]pyrrolo[2,1-c][1,4]benzodiazepine-2-carboxylic acid, ethyl ester: mp 187°-188° C. (cryst. from diethyl ether-hexane); Anal. Calcd for $C_{18}H_{17}N_3O_2$: C, 53.21% H, 4.96% N, 10.34%, Found: C, 53.27% H, 4.98% N, 10.26%; UV max (MeOH) 280 nm (ε16,000), 241 (24,200); NMR (CDCl$_3$)δ1.4 (t, 3H), 2.35 (s, 3H), 4.4 (q, 2H), 4.95 (s, 2H), 6.9 (m, 7H).

EXAMPLE 3

4-[(9H-Imidazo[1,2-a]pyrrolo[2,1-c][1,4]benzodiazepin-12-yl)thioxomethyl]morpholine [I: $R^1$ and $R^3$=H and $R^2$=(4-morpholinyl)thioxomethyl]

9H-Imidazo[1,2-a]pyrrolo[2,1-c][1,4]benzodiazepine (8.00 g, 36.1 mmoles) was heated in dry dimethylformamide (120 mL) at 120° C. in the presence of phosphoryl chloride (10.4 g, 6.32 mL). After 2 hours, the reaction mixture was poured onto ice-water and then extracted several times with chloroform. The combined extracts were washed with water, brine, dried and evaporation of solvent gave a tan residual solid. Crystallization of the solid form toluene-hexane gave 9H-imidazo[1,2-a]pyrrolo[2,1-c][1,4]benzodiazepine-12-carboxaldehyde (3.57 g): mp 203°-205° C.; Anal. Calcd for $C_{15}H_{11}N_3O$: C, 72.27% H, 4.45% N, 16.86%, Found: C, 72.08% H, 4.51% N, 16.77%.

A mixture of the latter compound (3.30 g, 13.3 mmoles), sulphur (1.52 g, 4.74 matg) and morpholine (25.41 mL) was heated with steam for 2 hr. The black solution was then diluted with ethanol (50 mL) and the solution was refluxed for 30 minutes. Upon cooling of the mixture in ice-water, a yellow precipitate was obtained. Recrystallization of the material from toluene-hexane afforded the title compound as yellow crystals (2.25 g): mp 210°-211° C.; Anal. Calcd for $C_{19}H_{18}N_4OS$: C, 65.12% H, 5.18% N, 15.99%, Found: C, 65.11% H, 5.31% N, 16.00% UV max (MeOH) 299 nm (ε19,300); NMR (CDCl$_3$)δ3.75 (t, 4H), 4.12 (m, 4H), 5.20 (m, 2H), 6.12 (d, 1H), 6.70 (d, 1H), 7.30 (m, 5H), 7.70 (m, 1H).

In the same manner but replacing morpholine with an equivalent amount of thiomorpholine, pyrrolidine, N-methylpiperazine or 1-(4-fluorophenyl)-piperazine, the following compounds of formula I were obtained, respectively: 4-[(9H-imidazo[1,2-a]pyrrolo[2,1-c][1,4]benzodiazepin-12-yl)thioxomethyl]-thiomorpholine: mp 202°-203° C. (cryst. from toluene-hexane); Anal. Calcd for C₁₉H₁₈N₄OS: C, 62.26% H, 4.95% N, 15.29%, Found: C, 61.42% H, 4.98% N, 14.89%; UV max (MeOH) 298 nm (ε18,430); NMR (DMSO-d₆)δ2.8 (m, 4H), 4.25 (br, 4H), 5.1 (s, 2H), 7.3 (m, 8H); 1-[(9H-imidazo[1,2-a]pyrrolo[2,1-a][1,4]benzodiazepin-12-yl)thioxomethyl]-pyrrolidine: mp 165°–166° C. (cryst. from toluene-hexane); Anal. Calcd for C₁₉H₁₈N₄S: C, 68.23% H, 5.42% N, 16.75%, Found: C, 68.17% H, 5.61% N, 16.38%; UV max (MeOH) 294 nm (ε18,030); NMR (DMSO-d₆)δ1.95 (m, 4H), 3.75 (m, 4H), 5.20 (s, 2H), 6.35 and 6.52 (doublets, 2H), 7.22 and 7.88 (doublets) 7.5 (m, 4H); 1-[(9H-imidazo[1,2-a]pyrrolo[2,1-c][1,4]benzodiazepin-12-yl)thioxomethyl]-4-methyl-piperazine: mp 205° C. (cryst. from toluene-hexane); Anal. Calcd for C₂₀H₂₁N₅S: C, 66.08% H, 5.82% N, 19.27%, Found: C, 66.73% H, 5.87% N, 19.10%; UV max (MeOH) 297 nm (ε19,300); NMR (DMSO-d₆)δ2.2 (s, 3H), 2.5 (m, 4H), 4.0 (m, 4H), 5.1 (S, 2H), 6.15 and 6.53 (doublets, 2H), 7.5 (m, 6H); and 4-(4-fluorophenyl)-1-[(9H-imidazo[1,2-a]pyrrolo[2,1-c][1,4]benzodiazepin-12-yl)thioxomethyl]-piperazine trihydrochloride: mp 275°–276° C. (cryst. from dimethylformamide-diethyl ether); Anal. Calcd for C₂₅H₂₂FN₅S.3HCl: C, 54.30% H, 4.55% N, 12.66%, Found: C, 54.70% H, 4.53% N, 13.00%; UV max (MeOH) 311 nm (ε20,500); 244 (25,000); NMR (DMSO-d₆)δ3.35 (m, 4H), 3.95 (m, 2H), 4.45 (m, 2H), 5.35 (s, 2H), 6.0 (br, 3H), 6.45 (d, 1H), 7.15 (m, 4H), 7.65 (m, 4H), 8.03 (d, 1H), 8.37 (d, 1H).

We claim:

1. A compound of the formula

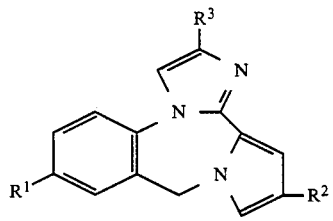

(I)

in which $R^1$ is hydrogen, halo or lower alkyl; $R^2$ is hydrogen or CS-$R^4$ wherein $R^4$ is 4-morpholinyl, 4-thiomorpholinyl, 1-pyrrolidinyl, 1-piperidinyl, 4-(lower alkyl)-1-piperazinyl or 4-(4-fluorophenyl)-1-piperazinyl; and $R^3$ is hydrogen or lower alkoxycarbonyl, or a therapeutically acceptable acid addition salt thereof.

2. A compound of claim 1 wherein $R^1$ is hydrogen, chloro or lower alkyl; $R^2$ is hydrogen or CS-$R^4$ wherein $R^4$ is 4-morpholinyl, 4-thiomorpholinyl, 1-pyrrolidinyl, 4-(lower alkyl)-1-piperazinyl or 4-(4-fluorophenyl)-1-piperazinyl; and $R^3$ is hydrogen or lower alkoxycarbonyl; with the proviso that when $R^2$ is CS-$R^4$ then $R^3$ is hydrogen, or a therapeutically acceptable acid addition salt thereof.

3. A compound of claim 1 wherein $R^1$ is hydrogen, chloro or methyl; $R^2$ is hydrogen or CS-$R^4$ wherein $R^4$ is 4-morpholinyl, 4-thiomorpholinyl or 4-(4-fluorophenyl)-1-piperazinyl with the proviso that when $R^2$ is CS-$R^4$ then $R^3$ is hydrogen; or a therapeutically acceptable addition salt thereof.

4. The compound of claim 2, which is 9H-imidazo[1,2-a]pyrrolo[2,1-c][1,4]benzodiazepine.

5. The compound of claim 2, which is 9H-imidazo[1,2-a]pyrrolo[2,1-c][1,4]benzodiazepine-2-carboxylic acid, ethyl ester.

6. The compound of claim 2, which is 7-chloro-9H-imidazo[1,2-a]pyrrolo[2,1-c][1,4]benzodiazepine-2-carboxylic acid, ethyl ester.

7. The compound of claim 2, which is 7-methyl-9H-imidazo[1,2-a]-pyrrolo[2,1-c][1,4]benzodiazepine-2-carboxylic acid, ethyl ester.

8. The compound of claim 2, which is 4-[(9H-imidazo[1,2-a]pyrrolo[2,1-c][1,4]benzodiazepine-12-yl)thioxomethyl]-morpholine.

9. The compound of claim 2, which is 4-[(9H-imidazo[1,2-a]pyrrolo[2,1-c][1,4]benzodiazepin-12-yl)thioxomethyl]-thiomorpholine.

10. The compound of claim 2, which is 1-[(9H-imidazo[1,2-a]pyrrolo[2,1-a][1,4]benzodiazepin-12-yl)thioxomethyl]-pyrrolidine.

11. The compound of claim 2, which is 1-[(9H-imidazo[1,2-a]pyrrolo[2,1-c][1,4]benzodiazepin-12-yl)thioxomethyl]-4-methyl-piperazine.

12. The compound of claim 2, which is 4-(4-fluorophenyl)-1-[(9H-imidazo[1,2-a]pyrrolo[2,1-c][1,4]benzodiazepin-12-yl)thioxomethyl]-piperazine trihydrochloride.

13. A pharmaceutical composition, which comprises a compound of claim 1, or a therapeutically acceptable acid addition salt thereof, and a pharmaceutically acceptable carrier.

14. A method of reducing food intake in a mammal, which comprises administering to the mammal an effective food intake reducing amount of a compound of claim 1, or a therapeutically acceptable acid addition salt thereof.

15. A process for preparing a compound of formula I

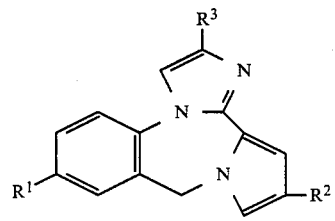

(I)

in which $R^1$ is hydrogen, halo or lower alkyl; $R^2$ is hydrogen or CS-$R^4$ wherein $R^4$ is 4-morpholinyl, 4-thiomorpholinyl, 1-pyrrolidinyl, 1-piperidinyl, 4-(lower alkyl)-1-piperazinyl or 4-(4-fluorophenyl)-1-piperazinyl; and $R^3$ is hydrogen or a therapeutically acceptable acid addition salt thereof, which comprises;

(a) condensing a compound of formula II

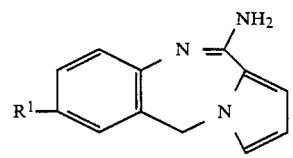

(II)

in which $R^1$ is as defined herein with aminoacetaldehyde dimethylacetal to obtain the corresponding compound of formula III

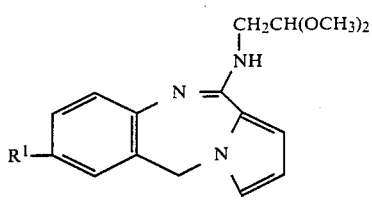

in which $R^1$ is as defined herein, and cyclizing the compound of formula III to obtain the corresponding compound of formula I in which $R^1$ is as defined herein, and $R^2$ and $R^3$ are hydrogen;

(b) reacting a compound of formula I in which $R^1$ is as defined herein and $R^2$ and $R^3$ are hydrogen with the Vilsmeier reagent to obtain the corresponding compound of formula V

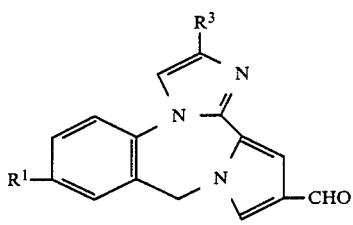

in which $R^1$ is as defined herein, and $R^3$ is hydrogen and reacting the compound of formula V with sulphur and one of the following amines: morpholine, thiomorpholine, pyrrolidine, piperidine, 4-(lower alkyl)-piperazine, 4-(4-fluorophenyl)-piperazine or di(lower alkyl)amine to obtain the corresponding compound of formula I in which $R^1$ is as defined herein, $R^3$ is hydrogen and $R^2$ is $CS-R^4$ wherein $R^4$ is as defined herein; and (c) reacting a compound of formula I in which $R^1$ and $R^2$ are as defined herein, and $R^3$ is hydrogen with a therapeutically acceptable acid to obtain the corresponding therapeutically acceptable acid addition salt of the compound of formula I in which $R^1$ and $R^2$ are as defined herein, and $R^3$ is hydrogen.

16. A process for preparing a compound of formula I

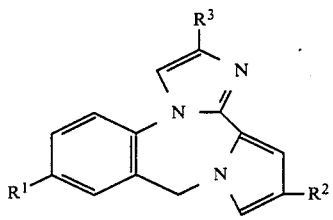

in which $R^1$ is hydrogen, halo or lower alkyl; $R^2$ is hydrogen or $CS-R^4$ wherein $R^4$ is 4-morpholinyl, 4-thiomorpholinyl, 1-pyrrolidinyl, 1-piperidinyl, 4-(lower alkyl)-1-piperazinyl or 4-(4-fluorophenyl)-1-piperazinyl; and $R^3$ is lower alkoxycarbonyl, or a therapeutically acceptable acid addition salt thereof, which comprises:

(a) condensing a compound of formula II

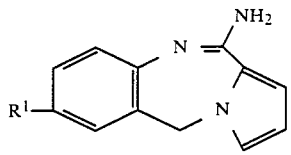

in which $R^1$ is as defined herein with a lower alkyl ester of bromo- or chloropyruvic acid to obtain the corresponding compound of formula IV (IV)

in which $R^1$ is as defined herein, Alk is lower alkyl and $X^-$ is bromide or chloride, and cyclizing the compound of formula IV to obtain the corresponding compound of formula I in which $R^1$ is as defined herein, $R^2$ is hydrogen and $R^3$ is lower alkoxycarbonyl;

(b) reacting a compound of formula I in which $R^1$ is as defined herein, $R^3$ is lower alkoxycarbonyl and $R^2$ is hydrogen with the Vilsmeier reagent to obtain the corresponding compound of formula V (V)

in which $R^1$ is as defined herein, and $R^3$ is lower alkoxycarbonyl and reacting the compound of formula V with sulphur and one of the following amines: morpholine, thiomorpholine, pyrrolidine, piperidine, 4-(lower alkyl)-piperazine, 4-(4-fluorophenyl)-piperazine or di(lower alkyl)amine to obtain the corresponding compound of formula I in which $R^1$ is as defined herein, $R^3$ is lower alkoxycarbonyl and $R^2$ is $CS-R^4$ wherein $R^4$ is as defined herein; and (c) reacting a compound of formula I in which $R^1$ and $R^2$ are as defined herein, and $R^3$ is a lower alkoxycarbonyl with a therapeutically acceptable acid to obtain the corresponding therapeutically acceptable acid addition salt of the compound of formula I in which $R^1$ and $R^2$ are as defined herein, and $R^3$ is a lower alkoxycarbonyl.

* * * * *